US00PP21198P2

(12) United States Plant Patent
Kordes

(10) Patent No.: US PP21,198 P2
(45) Date of Patent: Aug. 17, 2010

(54) SHRUB ROSE PLANT NAMED 'KORFLOCI01'

(50) Latin Name: *Rosa hybrida*
Varietal Denomination: KORfloci01

(75) Inventor: Tim-Hermann Kordes, Offenseth-Sparrieshoop (DE)

(73) Assignee: W. Kordes' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 100 days.

(21) Appl. No.: 11/893,517

(22) Filed: Aug. 15, 2007

(51) Int. Cl.
*A01H 5/00* (2006.01)

(52) U.S. Cl. ..... Plt./102

(58) Field of Classification Search ..... Plt./102
See application file for complete search history.

(56) References Cited

U.S. PATENT DOCUMENTS

PP14,334 P3 * 12/2003 Zary ..... Plt./102

OTHER PUBLICATIONS

UPOV ROM GTITM Computer Database. GTI Jouve Retrieval Software 2008/04 Citation for 'KORFLOCI01'.*
Cream Flower Circus available at: http://www.helpmefind.com/plant/l.php?1=2.46662.0&tab=1.*

* cited by examiner

*Primary Examiner*—Wendy C. Haas

(57) ABSTRACT

A new and distinct variety of rose with long lasting, novel light pink flowers, and attractive foliage with good disease resistance. It exhibits compact and uniform growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORfloci01'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1997. The crossing was between 'Taneitber', a non-patented rose and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORfloci01'.

SUMMARY OF THE INVENTION

The new rose plant may be distinguished from its seed parent, 'Taneitber', by the following combination of characteristics:

1. 'KORfloci01' has light pink flowers and 'Taneitber' has amber yellow flowers; and
2. 'KORfloci01' has a compact habit and 'Taneitber' has an upright habit.

The new rose plant may be distinguished from its pollen parent, an 'un-named seedling' by the following combination of characteristics:

1. 'KORfloci01' has a compact habit and the 'un-named seedling' has a spreading habit; and
2. The flowers of 'KORfloci01' are very double, while the flowers of the pollen parent are semi-double.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORfloci01' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORfloci01' was selected in May, 1998 from the seedling beds to be asexually propagated for further evaluation. The first asexual propagation of 'KORfloci01' was done by budding to seedling understocks in July, 1998 at the inventor's nursery in Offenseth-Sparrieshoop, Germany.

This initial and other subsequent propagations conducted in controlled environments demonstrate that 'KORfloci01' reproduces true to type in successive generations of asexual reproduction.

BRIEF DESCRIPTION OF THE DRAWING

The accompanying drawing, shows as true as is reasonably possible to obtain in color photographs of this type, the typical characteristics of the buds, flowers, leaves, and stems of 'KORfloci01'.

DETAILED BOTANICAL DESCRIPTION

The following is a description of 'KORfloci01', as observed growing in August, 2007 in a nursery in Jackson County, Oreg. on budded plants of 2 years of age. Color references are made using The Royal Horticultural Society (London, England) Colour Chart, 2001 except where common terms of color are used.

For a comparison, several physical characteristics of the rose variety 'KORgretaum', a patented rose variety from the same inventor described and illustrated in U.S. Plant Pat. No. 16,937 and issued on Aug. 1, 2006 are compared to 'KORfloci01' in Chart 1.

CHART 1

| Characteristic | 'KORfloci01' | 'KORgretaum' |
|---|---|---|
| Flower bud color, ¼ open | Upper surface: Yellow-Orange Group 21D. Lower surface, Yellow-Orange Group 22D. | Upper surface: White Group 157D. Lower surface: White Group 157D |
| Petal count. | Flower is double to very double, with 80 petals on average. | Flower is very double, with 75-80 petals, on average. |

Parents:

*Seed parent.*—'Taneitber'.

*Pollen parent.*—An un-named seedling.

Classification:

*Botanical classification.*—*Rosa hybrida,* 'KORfloci01'.

*Commercial classification.*—Shrub rose.

FLOWER AND FLOWER BUD

Blooming habit: Recurrent.

Flower bud:

*Size.*—Upon opening, 22-25 mm in length from base of receptacle to end of bud and 15-17 mm in diameter.

*Bud form.*—Short. Globular.

*Bud color.*—As sepals first unfold, bud color is Yellow-Orange Group 22D. When ¼ open, the upper surface of petals is Yellow-Orange Group 21D, and the lower surface is Yellow-Orange Group 22D with intonations of Orange Group 25D.

*Sepals.*—Size: Average 25 mm long×10 mm wide. Shape: Sepals generally subulate. Sepal apex is generally cirrose. Weak foliaceous appendages on three of the five sepals. Base is flat at union with receptacle. Quantity: Five. Surface texture: Inner side: Covered in fine hairs. Outer surface: Nearly smooth, with some fine hairs in the middle. Stipitate glands are present on the margins. Color: Upper surface Yellow-Green Group 146B. Lower surface Green Group 138A. Basal area: Yellow-Green Group 146D.

Receptacle:

*Surface.*—Smooth, with a few fine hairs.

*Color.*—Yellow-Green Group 146C.

*Shape.*—Funnel shaped.

*Size.*—5-6 mm (h)×7-8 mm (w).

Peduncle:

*Surface.*—With limited numbers of fine hairs and stipitate glands.

*Length.*—22-25 mm average length.

*Diameter.*—1.25-1.5 mm average diameter.

*Color.*—Yellow-Green Group 146C.

*Strength.*—Moderately strong, with some flowers nodding.

*Borne.*—Multiple flower buds per stem, generally 1 to 3.

Flower bloom:

*Fragrance.*—Light floral scent.

*Duration.*—On the plant 3-4 days. Senesced petals drop away cleanly.

*Size.*—Medium flowered garden rose. Average flower diameter is 55 mm when open.

*Form.*—Shape of flower when viewed from the side: Upon opening, upper part: Flattened convex. Upon opening, lower part: Flattened convex. Open flower, upper part: Flat. Open flower, lower part: Flat.

Color:

*Upon opening, petals.*—Outermost petals: Outer Side: Orange Group 23D. Inner Side: Orange Group 23D. Innermost petals: Outer Side: Orange Group 24D. Inner Side: Orange Group 24D.

*Upon opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D.

*After opening, petals.*—Outermost petals: Outer Side: Orange Group 27C. Inner Side: Orange Group 27C. Innermost petals: Outer Side: Orange Group 24D and Orange Group 27D. Inner Side: Orange Group 24D and Orange Group 27D.

*After opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D. Variegations: None.

General tonality: On open flower, general tonality is a blend of Orange Group 27C and Orange Group 27D. No change in the general tonality at the end of the 3$^{rd}$ day. Thereafter, general tonality transitions to Orange-White Group 159B.

Petals:

*Petal count.*—Approximately 80 petals under normal conditions.

*Petal reflex.*—Petals reflex somewhat.

*Petal edge.*—With point in center of margin.

*Petal shape.*—Apex shape is round. Shape of base is acute to rounded.

*Petal size.*—Variable. 18-35 mm long; 12-28 mm wide.

*Thickness.*—Average.

*Petal arrangement.*—Generally in a regular pattern with overlapping edges.

*Petaloids.*—Present. Average of 20 per flower. Surface texture is smooth. Shape is linear to elliptic.

Reproductive organs:

*Pistils.*—Flowers are incomplete. Approximately 15 present. Stigmas: Color: White Group 157A. Styles: Length: 5 mm long. Color: Yellow-Green Group 154A. Intonations of Greyed-Red Group 180C.

*Stamens.*—Flowers are lacking stamens.

THE PLANT

Plant growth: Moderate vigor. Compact. When grown as a budded nursery plant the average plant height is 60 cm and the average plant width is 60 cm.

Stems:

*Stem color.*—Young wood: Yellow-Green Group 146C. Older wood: Yellow-Green Group 146C.

*Stem surface.*—Young wood: Smooth. Older wood: Smooth.

Prickles: Present.

*Incidence.*—4-5 per 10 cm of stem.

*Size.*—Average length: 7 mm.

*Color.*—Immature prickles: Yellow-Green Group 146D. Mature prickles: Greyed-Orange Group 173C. Senescing to Greyed-Orange Group 173D. Anthocyanin intonations: Green Group 180C.

*Shape.*—Linear.

Leaves and leaflets: Normally 5 leaflets on normal leaves in middle of the stem.

*Leaf size.*—110 mm (l)×75 mm (w).

*Quantity.*—Average to above average.

*Texture.*—Upper side of leaflet: Glossy and smooth. Under side of leaflet: Semi-glossy, smooth, and leathery.

*Color, mature foliage.*—Upper Leaf Surface: Green Group 132A. Lower Leaf Surface: Green Group 138A.

*Color, juvenile foliage.*—Upper Leaf Surface: Green Group 137A. Lower Leaf Surface: Green Group 138A.

*Anthocyanin intonation.*—Present. Location: Light intonations present on juvenile leaf margins, developing leaves, peduncles, and stems.

Stipules:

*Size.*—12 mm (l) — 5 mm (w)

*Stipule color.*—Green Group 138A. .

*Presence of stipitate glands.*—A few on margins.

*Margins.*—With stipitate glands.

Petiole:

*Length.*—15 mm.

*Diameter.*—1.2 mm.

*Petiole color.*—Green Group 138A.

*Underneath.*—Smooth.

*Stipitate glands.*—Limited numbers of stipitate glands on margins.

Petiole rachis:

*Length.*—25 mm.

*Diameter.*—1.2 mm.

*Color.*—Green Group 138A.

*Margins.*—Smooth.

*Prickles.*—Occasional.

*Stipitate glands.*—Limited numbers of stipitate glands on margins.

Leaflets:

*Size.*—Average size of the terminal leaflet is 40 mm (l)×30 mm (w).

*Surface color.*—Upper: Green Group 137A. Lower: Green Group 138A.

*Leaflet shape.*—Base: Ovate. Apex: Ovate.

*Margins.*—Serrated.

*Texture.*—Thick.

Hips/seed formation: None observed.

Winter hardiness: To date, the variety has been grown successfully in Zone 5.

Disease resistance: Excellent resistance to powdery mildew, rust, Botrytis, disease under normal growing conditions.

The invention claimed is:

1. A new and distinct variety of rose plant, as herein illustrated and described.

* * * * *

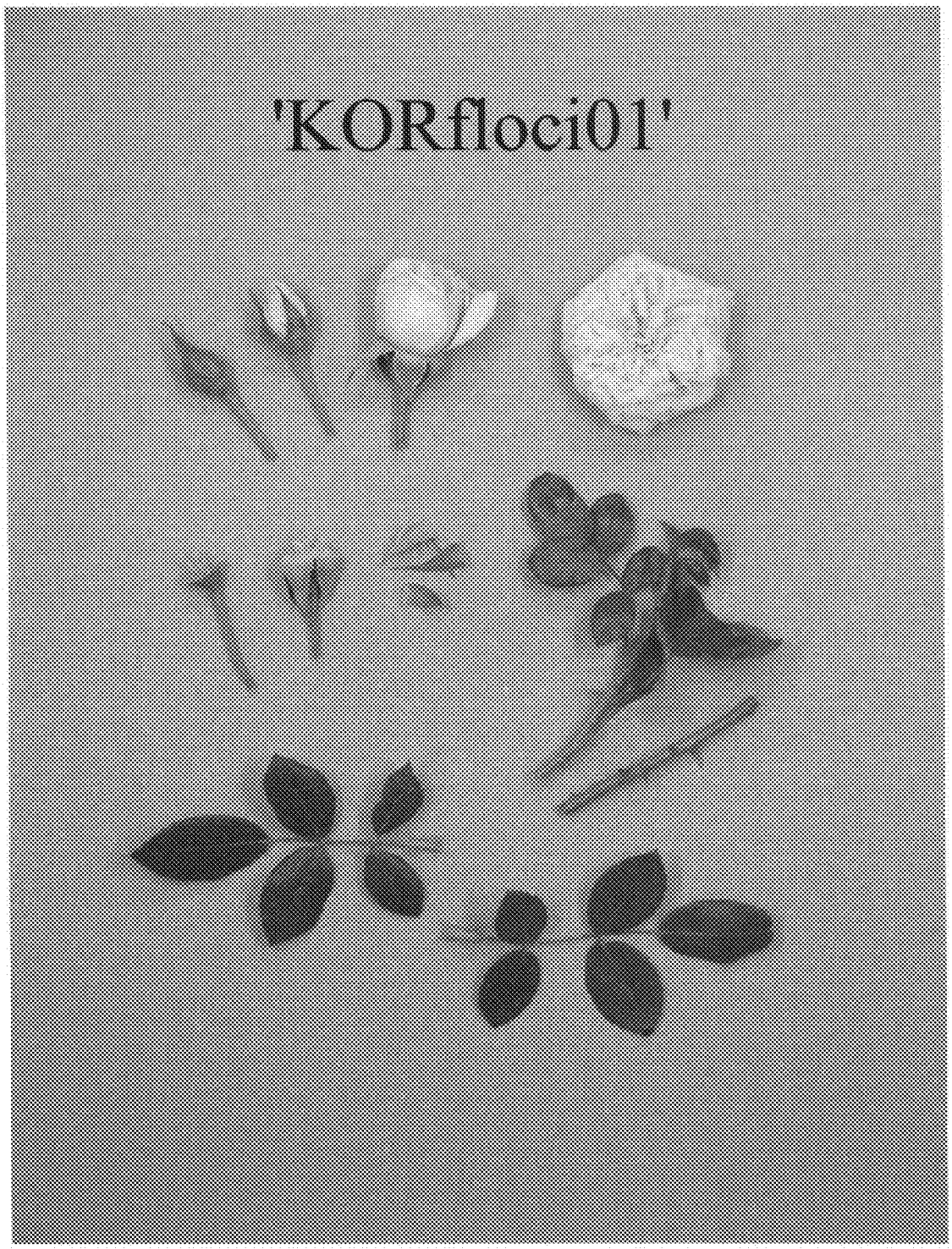
'KORfloci01'